(12) United States Patent
Walker

(10) Patent No.: US 6,457,348 B1
(45) Date of Patent: Oct. 1, 2002

(54) HIGH PRESSURE STEAM LINE TARGET INSERTER

(75) Inventor: David R. Walker, Houston, TX (US)

(73) Assignee: Onyx Industrial Services, Inc., La Porte, TX (US)

( * ) Notice: Subject to any disclaimer, the term of this patent is extended or adjusted under 35 U.S.C. 154(b) by 2 days.

(21) Appl. No.: 09/813,248

(22) Filed: Mar. 20, 2001

(51) Int. Cl.$^7$ ................ G01N 11/00; B01D 41/00; B08B 9/00

(52) U.S. Cl. ............ 73/60.11; 134/22.12; 96/228

(58) Field of Search ............... 73/60.11, 865.8; 134/22.12, 22.15, 22.18, 30, 37; 261/DIG. 54, DIG. 76; 96/228, 188, 311, 321, 356

(56) References Cited

U.S. PATENT DOCUMENTS

| 4,853,014 A | 8/1989 | Bloch |
| 4,921,546 A | 5/1990 | Bloch |
| 4,922,937 A | 5/1990 | Bloch |

*Primary Examiner*—Hezron Williams
(74) *Attorney, Agent, or Firm*—Kenneth A. Keeling; Keeling Hudson L.L.C.

(57) ABSTRACT

A high-pressure high-velocity target inserter for use in steam cleaning. The target inserter uses an actuator connected to a tube assembly, which connects to a test line. The target inserter uses packing to prevent high-pressure steam from being released through the target inserter when the target rod is inserted and withdrawn from the line. In the preferred embodiment, the target rod passes through a remotely operated actuator controlled valve and a remotely controlled actuator controller, such that the operator is kept a safe distance away from the inserter when the access valve to the line is open.

20 Claims, 5 Drawing Sheets

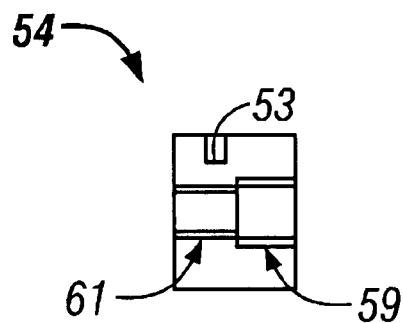
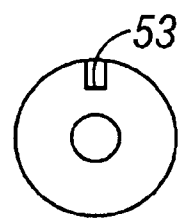
FIG. 2A  FIG. 2B
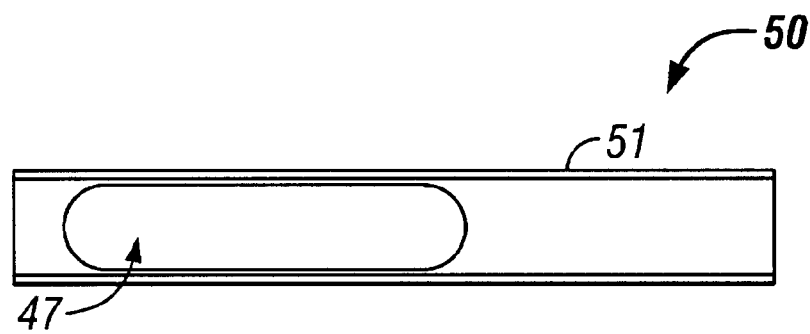
FIG. 3A
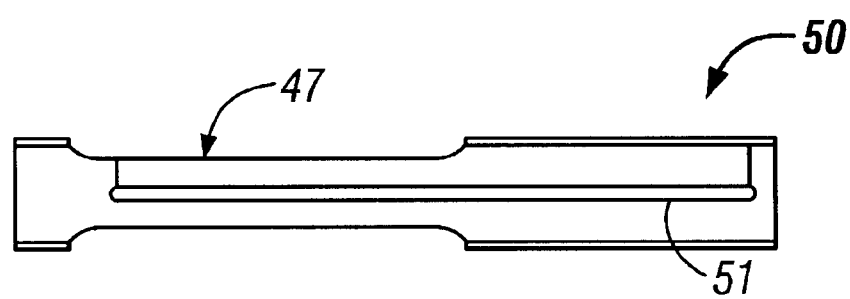
FIG. 3B

HIGH PRESSURE STEAM LINE TARGET INSERTER

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of Invention

This invention relates to a method and device for determining the level of cleanliness in a pipe, conduit and the like. Specifically, the invention describes a target inserter for use with high-pressure high-velocity fluids (steam, liquid, air or similar cleaning fluids).

2. Related Art

Piping, conduits, vessels and similar structures are used in a variety of manners. Typically, such conduits are used to transport fluid materials, such as hydrocarbons, brine, and other liquids used in chemical and petrochemical processes. Similarly, such conduits may be used to transport fuels, including gas and liquid hydrocarbons. Conduits in other applications include those used to provide power steam in turbines. Typically, over time the interior surfaces of such piping frequently become coated with scale and other buildup of the transported material or its by-products. These deposits on the walls of the interior of the conduits pose a variety of problems, depending on the conduit and its use. For example, debris such as scale in a steam line may become dislodged, causing severe damage to steam turbine blades when struck by the entrained debris in the high velocity steam line. Buildup on the walls of piping in a heat exchanger reduce the efficiency in the heat transfer, including irregular heat transfer that may result in inefficient chemical reactions. Buildup on the walls of feedstock or fuel line in a petrochemical process may result in turbulence or blockage in the line, reducing the efficiency of the process until it is forced to shut down.

In a petrochemical or similar processing unit, cleaning of the lines cannot be accomplished while the unit is in operation. The unit must be shut down for such maintenance, referred to typically as a "turnaround". Normally closed loop systems are drained of their contents, purged if necessary, and cleaned out. A common method of cleaning out the lines is with high velocity steam. High temperature steam is flushed through the lines at high velocity, mechanically breaking off and flushing the built-up material on the wall interior. Cavitation often occurs as the high-velocity steam passes through the conduit, thus aiding in the breaking up of the build-up slag away from the vessel walls.

In the prior art, such as described by Bloch in U.S. Pat. No. 4,853,014, low-pressure high-velocity steam is used for interior cleaning of pipes. Pressure is built up in a boiler, and then released through the lines to be cleaned. The lines are then allowed to cool while steam pressure is built up again in the boiler. This blow cycle is repeated until the line is clean. To determine if the steam (and therefore the line) is clean, a piece of soft metal called a target is supported across the interior of the terminal portion of the line. The target is inserted into the line (typically between blow cycles), steam is blown through the line, and the target then removed. Pits in the metal target are caused by debris from the line striking the metal. These pits are counted to quantify the level of cleanliness of the line. When the line is still "dirty", numerous pits are observed. As the line becomes cleaner, there are fewer small debris particles being pushed by the steam, and thus there are fewer pits in the target. The steam is then vented out the line through an expansion chamber, into which Bloch introduces a decelerating mist for noise control. While this method takes advantage of the flushing and cavitational forces provided by steam at near sonic velocity, being at low pressure requires a high volume of water to adequately flush out the line. Further, target insertion/removal must be performed at low pressure, typically between blow cycles, due to the prior art design limitations of the target inserter. Finally, the steam can only be used in a single unit, since there is inadequate pressure to pipe the steam to a second unit to clean it as well.

A preferred method of cleaning pipes, conduits and like devices is to use a high-pressure high-velocity gas stream, typically steam. While the term "steam" will be used throughout the description of the prior art and this invention, it is understood that "steam" is to encompass all similar gas streams used in the context of pressure cleaning.

Using a high-pressure gas stream offers several advantages over low-pressure. First, since most systems being cleaned normally operate at high pressure, they respond best to a high-pressure cleaning gas stream. Such systems often have bends and recesses in their interior structure of the conduits. As such, the normal fluid traveling through the piping hits and impinges on areas within the conduit that may be restricted. A low-pressure gas stream will not invade such spaces, but will pass over these areas. Therefore, a high-pressure gas stream that mimics the pressure and characteristics of the material within the conduit during normal operation will provide better cleaning access to all areas within the conduit. Second, low-pressure gas streams rely heavily on the force of relatively high volume of water to flush out the conduit being cleaned. The water used is typically demineralized, and is relatively expensive compared to untreated water. Further, this high volume of water must be treated after being flushed through the conduit, which often contains hazardous materials. Treatment of this effluent water is often expensive and resource consuming. Finally, high-pressure steam can be used to clean more than one unit. By connecting more than one unit of conduits with a temporary connection line, steam used to clean the first unit can continue through the temporary connection to flush through the second unit.

While the advantages of using high-pressure high-velocity steam are clear, such steam has not been used due to technical and safety problems associated with the target. As described above, a target is used to determine the cleanliness of the conduit by determining the cleanliness of the steam. By determining the cleanliness of the steam, it is assumed that the interior of the conduit being cleaning is analogously clean, having had all friable and loose scale knocked off by the steam. When using the same steam to clean a second unit that was used in a first unit (using temporary connection piping as described above), a method and device are needed to determine the cleanliness of the first unit as well as the second unit. If the target is only placed at the exit of the second unit piping, the source of debris causing pitting on the target is unknown, since it could come from the first unit or the second unit. Thus a target inserter between the first unit and second unit is needed to measure the cleanliness of the first unit. The cleanliness of the second unit is then determined by subtracting the number of pits from the first unit's target from the number of pits from the second unit's target.

It would therefore be useful improvement of the prior art of target inserters to be able to function in a high-pressure high-velocity steam environment while the cleaning system is still under high pressure.

BRIEF SUMMARY OF THE INVENTION

Accordingly, the objectives of this invention are to provide, inter alia, a new and improved target inserter for use in determining the cleanliness of a pipe, conduit and like device being cleaned by a high-pressure high-velocity gas stream cleaning system. These objectives include having a device and system that:

operates at high pressure;

utilizes standard metal targets and target rods;

can be remotely operated for increased safety; and connects to standard pipe flanges and valves.

These objectives are addressed by the structure and use of the inventive device. Other objects of the invention will become apparent from time to time throughout the specification hereinafter disclosed.

BRIEF DESCRIPTION OF THE DRAWINGS

FIGS. 2A and 2B depict a coupler for connecting a target rod and an actuator rod.

FIGS. 3A and 3B depict a sleeve assembly for holding a target rod.

DETAILED DESCRIPTION OF THE INVENTION

Figure 1:
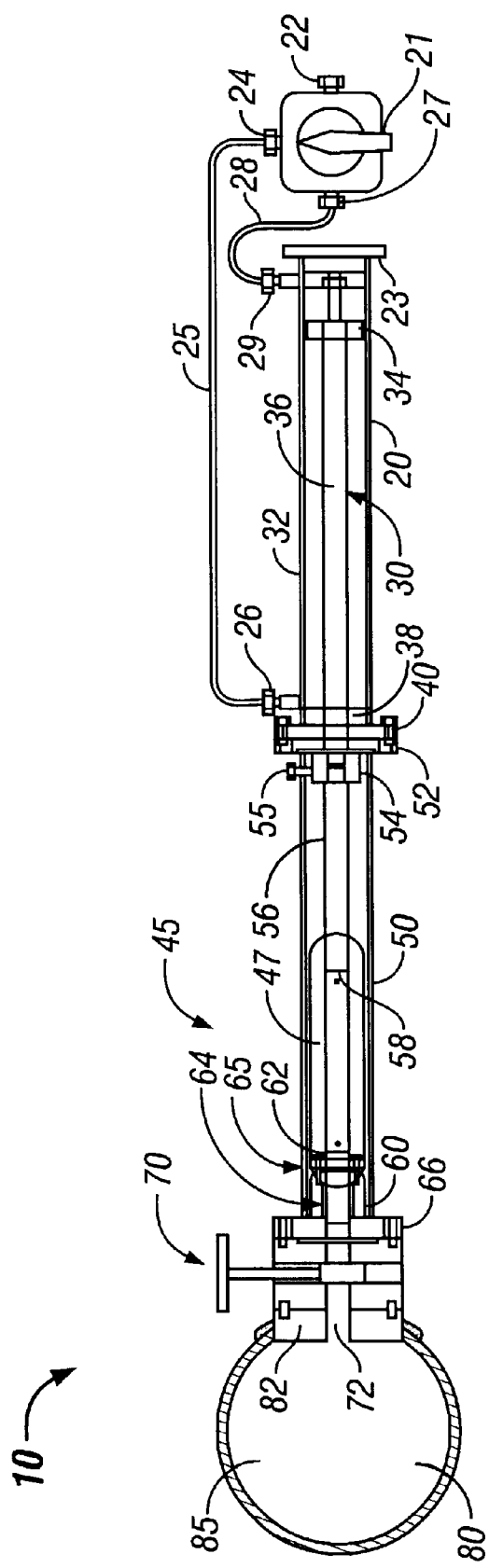
FIG. 1 depicts the preferred embodiment of the inventive high-pressure target inserter.

The present invention is described as target inserter 10, depicted in the preferred embodiment in FIG. 1.

Actuator 40 is attached to sleeve assembly 50. Shell assembly 45 includes sleeve assembly 50, which has a first end and a second end. The first end of shell assembly 45 connects to actuator 20. In the preferred embodiment, this attachment is accomplished by bolting actuator flange 40 to actuator adapter flange 52, which is preferably a 150# flange welded to sleeve assembly 50. The second end of shell assembly 45 is connected either directly or indirectly to pipe 80. If directly connected, the second end of shell assembly 45 is connected to a flange welded to the side wall of pipe 80, the flange being circumferential to an opening in the wall of pipe 80. If indirectly connected to pipe 80, as in the preferred embodiment, the second end of shell assembly 45 is connected to a valve 70, which is bolted to the flange welded to the side wall of pipe 80. This valve 80 has flanges on each end allowing it to be bolted to the pipe flange and packing gland housing flange 66, which is located at the second end of shell assembly 45, as depicted in FIG. 1. Actuator piston 30 is connected to actuator/rod coupling 54, located within shell assembly 45 as shown in FIG. 1. Actuator/rod coupling is shown detail in FIGS. 2A and 2B.

Typically, actuator piston 30 is connected to actuator/rod coupling 54 by screwing actuator piston 30 into actuator piston receiving threaded hole 59 of actuator/rod coupling 54 until tight.

Actuator 20 comprises actuator piston 30, which is oriented within actuator housing 32. Actuator piston 30 comprises actuator piston rod 36, which attaches at one end to actuator/rod coupling 54, and at the other end connects to actuator piston head 34. Between actuator piston head 34 and actuator end cap 23 is actuator extend air inlet 29. Actuator extend air inlet 29 is connected to extend pneumatic hose 28, which connects to actuator controller extend air outlet 27. Actuator extend air inlet 29, extend pneumatic hose 28 and actuator controller extend air outlet 27 provide pneumatic communication between actuator pneumatic controller 21 and the cavity interior to actuator housing 32 between actuator piston head 34 and actuator end cap 23.

Actuator cylinder seal 38 is located in the interior of actuator 20, and provides a pneumatic seal between the interior of actuator housing 32 and actuator flange 40, while allowing passage of actuator piston 30 therethrough. Between actuator piston head 34 and actuator cylinder seal 38 is actuator retract air inlet 26. Actuator retract air inlet 26 is connected to retract pneumatic hose 25, which connects to actuator controller retract air outlet 24. Actuator retract air inlet 26, retract pneumatic hose 25 and actuator controller retract air outlet 24 provide pneumatic communication between actuator pneumatic controller 21 and the cavity interior to actuator housing 32 between actuator piston head 34 and actuator cylinder seal 38.

Actuator pneumatic controller 21 is a standard pneumatic controller having actuator controller air inlet 22, actuator controller retract air outlet 24, actuator controller extend air outlet 27 and means for directing pressurized air coming into actuator controller air inlet 22 to actuator controller retract air outlet 24 or actuator controller extend air outlet 27. When pressurized air is directed to actuator controller extend air outlet 27, pressure from retract pneumatic hose 25 and actuator retract air inlet 26 is allowed to bleed off through actuator controller retract air outlet 24. Conversely, when pressurized air is directed to actuator controller retract air outlet 24, pressure from extend pneumatic hose 28 and actuator extend air inlet 29 is allowed to bleed off through actuator controller extend air outlet 27. For safety purposes, this transition between pressurizing and bleeding off pressure between the retract and extend systems is gradient, to that the rate of extension/retraction can be controlled, preventing a "blow-out" of the actuator piston from uncontrolled pressure against target rod 56.

Target rod 56 is attached to target rod receiving threaded hole 61 of actuator/rod coupling 54, as shown in FIG. 1. Details of actuator/rod coupling 54 are shown in FIGS. 2A and 2B. Actuator/rod coupling 54 has three threaded holes. The first is actuator piston receiving threaded hole 61, into which actuator piston rod 36 is screwed. The preferred dimensions of actuator piston receiving threaded hole 59 are approximately 1¼"-12 THD×1⅛ deep. The second is target rod receiving threaded hole 61, into which target rod 56 is screwed, being axial with actuator piston receiving threaded hole 61 and actuator piston rod 36. The preferred dimensions of target rod receiving threaded hole 61 are approximately 1"-12 THD×1⅛" deep. The third is flag bolt receptor 53, which is cut into the top rounded surface of actuator/rod coupling 54, and oriented normal to target rod receiving threaded hole 61. In the preferred embodiment, flag bolt receptor 53 is a threaded hole, having preferred dimensions of approximately ½"-13 THD×¾" deep. Flag bolt receptor 53 receives flag bolt 55.

Flag bolt 55 serves two main purposes. First, it prevents rotation of actuator/rod coupling 54, so that actuator piston 30 and/or target rod 56 do not become unscrewed by such rotation. Second, flag bolt 55 serves as a visual indicator showing if target 58 is inserted within test pipe 80. Flag bolt 55 traverses through flag bolt slot 51, shown in FIGS. 3A and 3B. Flag bolt slot 51 is a slot, preferably approximately ½" wide, oriented along the longitusdinal axis of sleeve assembly 50. When target 50 is inserted into pipe interior 85 of pipe 80, flag bolt 55 is in a first position proximate pipe 80. When target 50 is withdrawn from pipe interior 85, flag bolt 55 is in a second position distal pipe 80. Thus a quick visual reference is provided to show if it is safe to open or close valve 70 depending on where target 58 and target rod 56 are oriented.

Figure 4A:
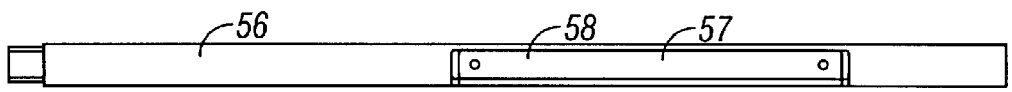
FIGS. 4A and 4B depict a target rod.
Figure 4B:
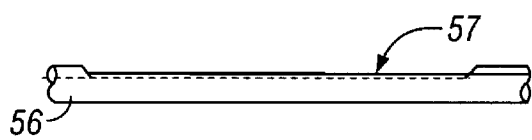
Figure 5:
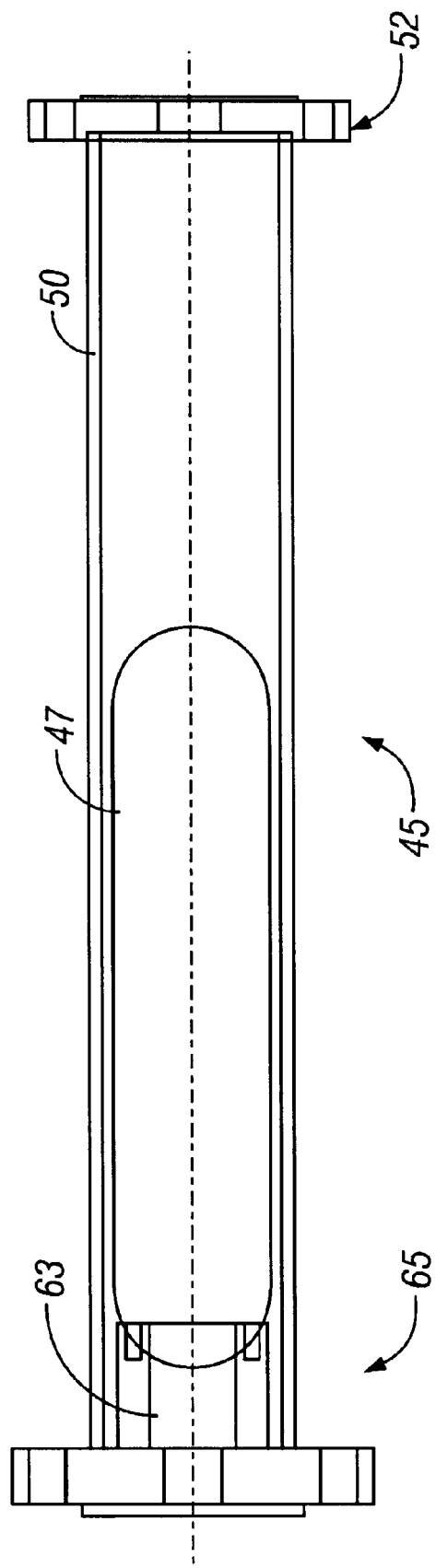
FIG. 5 depicts a shell assembly, including a sleeve assembly and connection flanges.

Target rod 56, shown in detail in FIGS. 4A and 4B, is oriented along the central axis of the longitudinal interior of shell assembly 45. Shell assembly 45, depicted in detail in FIG. 5, comprises sleeve assembly 50, packing head housing 65, actuator adaptor flange 52 and target access 47. Target access 47 is a void cut into at least one side of sleeve assembly 50, and allows access to target recess 57 for connecting, typically with screws, target 58 to target rod 56. Target rod 56 is preferably comprised of a strong metal, such as 4140 stress relieved steel. Target rod 56 comprises a threaded end for attachment to actuator/rod coupling 54 as described above, plus a target recess 57. Target recess 57 has a flat surface, against which target 58 mates and is attached, typically with screws into threaded holes located in the flat surface of target recess 57. To provide access to target recess 57, target rod 56 is aligned as in FIG. 1, such that target recess 57 faces out through a target access 47.

Figure 6A:
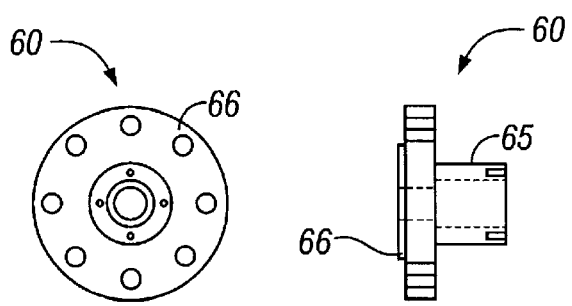
FIG. 6A depicts a packing head used in a shell assembly.
Figure 6B:
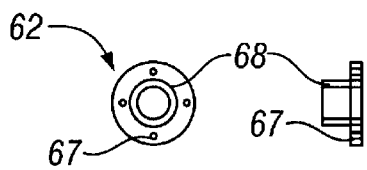
FIG. 6B depicts a packing gland used with a packing head for pressing packing against a target rod.

Target rod 56 traverses through packing head 60, which is oriented at the end of shell assembly 45 proximate to an opening in a wall of pipe 80 and distal to actuator 20. Packing head 60 comprises packing gland 62, packing cavity 63, packing 64, packing gland housing 65, and packing gland housing flange 66. Packing 64, typically multiple packing rings, is oriented within packing cavity 63 and circumferentially around target rod 56. Packing gland flange 67 of packing gland 62 bolts onto packing head 60 of into packing gland housing 65, such that packing gland sleeve 68 inserts into packing cavity 63 of packing gland housing 65, thus pressing packing 64 against target rod 56 when tightened. The preferred embodiment of packing gland housing 65 and packing gland 62 are depicted in FIGS. 6A and 6B. Packing gland housing flange 66 connects, typically with bolts, to valve 70, which is connected to pipe flange 82. Pipe flange 82 is oriented axial to an opening in the wall of pipe 80. Target rod 56 and target 58 are able to traverse through valve channel 72 when valve 70 is open. Valve 70 is typically a gate valve. In the preferred embodiment, valve 70 is opened and closed by a remotely controlled valve actuator, to provide additional safety to the operator. Alternatively, shell assembly 45 can be attached directly to an opening in the wall of pipe 80 where there is a point of attachment, such as a flange, attached directly to the side of pipe 80 around the wall opening. However, this alternatively embodiment does not offer the same safety advantage offered by the use of valve 70 as an attachment to pipe 80 for access to pipe interior 85.

OPERATION

Figure 7:
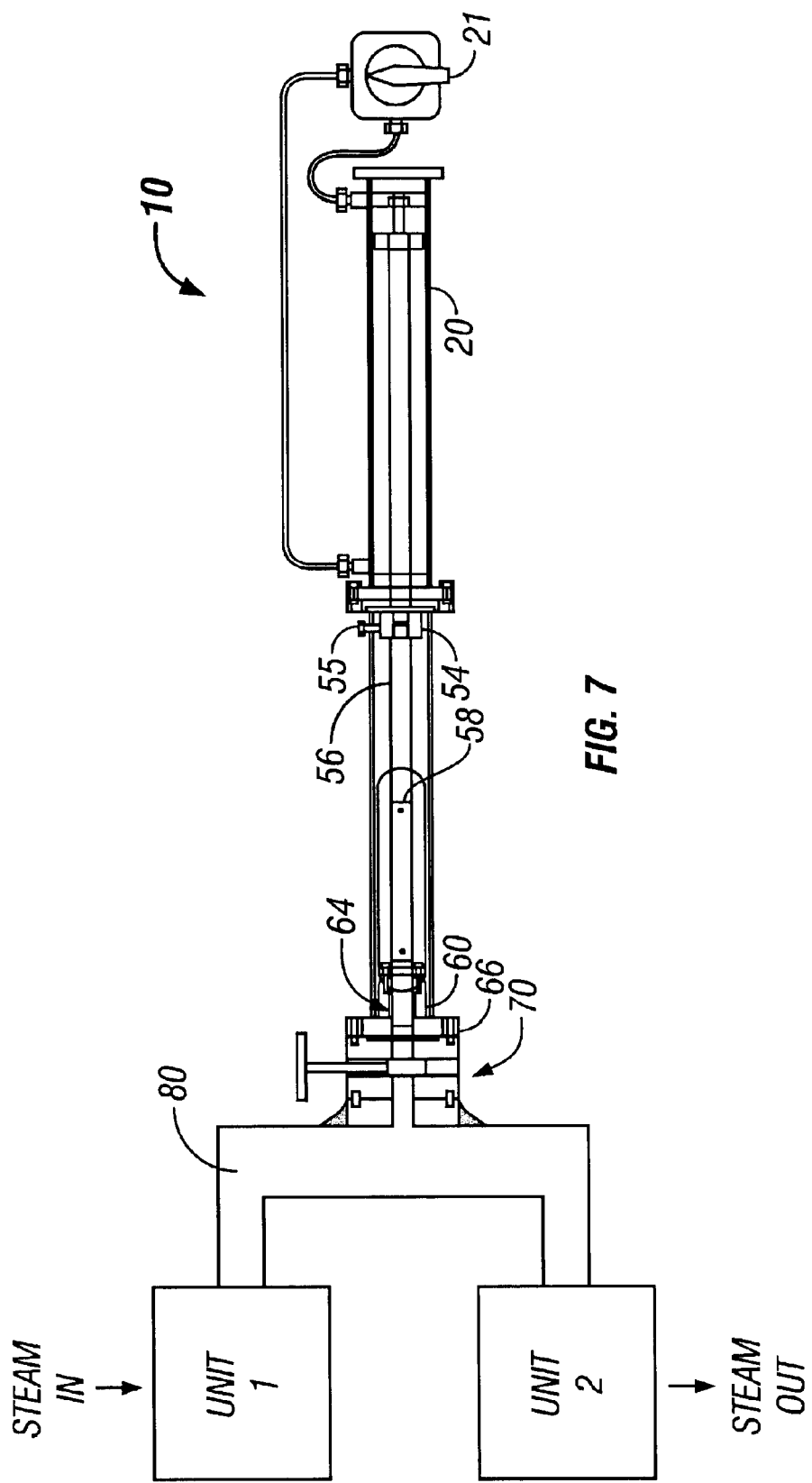
FIG. 7 depicts in graphic and illustrative form the inventive target inserter used in the preferred embodiment between two units being cleaned by the same high-pressure high-velocity gas.

Target inserter 10 may be used in any steam cleaning system, including those using high-pressure high-velocity steam. In the preferred embodiment shown in FIG. 7, target inserter 10 is connected to pipe 80, which is a temporary connection between Unit 1 and Unit 2. Unit 1 and Unit 2 are any systems having piping, conduit, vessels and the like to be cleaned by high-pressure high-velocity gas such as steam. High-pressure high-velocity steam is introduced into the piping system of Unit 1. This steam exits Unit 1 into temporary pipe 80. The steam (still at high-pressure and high-velocity) then enters the piping system of Unit 2, from which the steam ultimately exhausts to the atmosphere or a retention system (in the case of hazardous materials in the units). The high-pressure high-velocity steam travels through the piping of Unit 1, cleaning out debris from the interior walls of the piping. This steam and its accompanying debris flush through the piping of Unit 1, through temporary pipe 80, and then through the piping of Unit 2.

To determine the cleanliness of the steam exiting Unit 2, the inventive target inserter 10 or a prior art inserter typically may be used, since the steam being exhausted from Unit 2 is typically at low pressure. To determine the cleanliness of steam exhausting from Unit 1 and passing through temporary pipe 80 to Unit 2, inventive target inserter 10 must be used, since the steam is still at high pressure.

Target inserter may be used where pressure exceed normal steam blow cleaning pressures of 10 to 75 PSIG. Target inserter 10 will function at pressures up to 600 PSIG and maintain operator safety by sealing escaping steam via packing 64, and thereby preventing blowback. To assemble target inserter 10, actuator 20 is first attached to shell assembly 45 by connecting, typically with bolts, actuator flange 40 and actuator adapter flange 52. In the preferred embodiment, actuator adapter flange 52 is a 3"-150 flange. Using low-pressure air, actuator piston rod 36 is extended by directing air through actuator pneumatic controller 21 to actuator extend air inlet 29. The threaded end of actuator piston rod 36 is screwed into actuator piston receiving threaded hole 59 of actuator/rod coupling 54 and tightened. Actuator piston 30 is then retracted into actuator 20. Packing 64 (typically multiple rings of packing) are inserted into packing cavity 63 and packing gland 62 is lightly attached to packing head 60. The threaded end of target rod 56 is passed through packing head 60 and screwed into target rod receiving threaded hole 61 of actuator/rod coupling 54. Actuator/rod coupling 54 is oriented such that flag bolt receptor 53 is normal to flag bolt slot 51, and flag bolt 55 is then inserted and tightened into flag bolt receptor 53 on actuator/rod coupling 54. Target rod 56 is aligned such that target recess 57 is oriented outward through target access 47. Packing gland 62 is then tightened until it gently squeezes target rod 56.

Packing gland housing flange 66 is then attached to closed valve 70. Target 58 is attached to target rod 56 in target recess 57. Pressurized air is connected to actuator controller air inlet 22 while actuator pneumatic controller 21 is in the "Retract" position. Target inserter is now ready for use.

Closed valve 70, attached to pipe 80, is opened, preferably remotely using a standard remote controlled valve actuator mechanism. Actuator 20 is extended, pushing target rod 56 and target 58 through the valve channel 72 of open valve 70, and then into pipe interior 85 of pipe 80. Target 58 is oriented normal to the flow path of the high-pressure high-velocity steam in pipe 80. Thus the steam and debris particles carried by the steam impinge against target 58, forming a quantifiable number of pits in target 58. After a determined length of time, actuator pneumatic controller 21 is engaged to retract target rod 56 and target 58 out of pipe interior 85 and through valve channel 72. After retraction, valve 70 is closed for additional safety, and target 58 removed for analysis. A fresh target 58 is installed, and the process repeated until the high-pressure high-velocity steam and lines it has cleaned are determined to be adequately clean.

The foregoing disclosure and description of the invention is illustrative and explanatory thereof. Various changes in the details of the illustrated construction may be made within the scope of the appended claims without departing from the spirit of the invention. The present invention should only be limited by the following claims and their legal equivalents.

I claim:

1. A high-pressure target inserter, comprising;
    a shell assembly having a first end and a second end;
    an actuator comprising an actuator piston;
    said actuator connecting to said first end of said shell assembly;
    said shell assembly comprising a sleeve assembly, a target rod, a target, and a packing gland housing;
    said target attached to said target rod;
    said packing gland housing proximate said second end of said shell assembly;
    said target rod connected to said actuator piston; and
    said second end of said shell assembly connected to an opening in a pipe wall of a pipe.

2. The high-pressure target inserter as in claim 1, wherein:
    said packing gland housing comprising a packing, a packing gland, and a packing gland housing flange;
    said packing oriented within said packing gland housing;
    said packing surrounding a circumference of and contiguous with said target rod;
    said packing gland pressing said packing against said target rod; and
    said target rod being slidingly movable through said packing and through said pipe wall opening into an interior of said pipe.

3. The high-pressure target inserter as in claim 2, further comprising:
    a valve having a first end and second end;
    said first end of said valve connected to said pipe wall opening;
    said packing gland housing connected to said second end of said valve; and
    said target rod being slidingly movable through a valve channel interior said valve and through said pipe wall opening into said interior of said pipe.

4. The high-pressure target inserter as in claim 3, said valve being remotely operable.

5. The high-pressure target inserter as in claim 4, said valve being operable by a valve actuator.

6. The high-pressure target inserter as in claim 3, said pipe wall opening comprising a flange capable of attaching to said first end of said valve.

7. The high-pressure target inserter as in claim 1, further comprising:
    a flag bolt slot oriented along a longitudinal axis of said sleeve assembly;
    a flag bolt traversing through said flag bolt slot and connecting to a actuator/rod coupling;
    said actuator/rod coupling connecting said target rod and said actuator piston;
    wherein said flag bolt is oriented proximate said second end of said shell assembly when said target rod is inserted into said pipe interior; and
    said flag bolt is oriented proximate said first end of said shell assembly when said target rod is withdrawn from said pipe interior.

8. The high-pressure target inserter as in claim 2, said actuator further comprising a remotely controlled pneumatic controller capable of extending and retracting said target into said pipe interior.

9. The high-pressure target inserter as in claim 1, said sleeve assembly further comprising a target access void.

10. The high-pressure target inserter as in claim 1, said pipe connecting a first set of conduits to be cleaned and a second set of conduits to be cleaned by a high-pressure high-velocity fluid.

11. A method of assessing the cleanliness of a high-pressure high-velocity fluid in a pipe, comprising:
    connecting a high-pressure target inserter to a side opening in a pipe having a pipe interior under high-pressure, said target inserter comprising a shell assembly having a first end and a second end; an actuator comprising an actuator piston; said actuator connecting to said first end of said shell assembly; said shell assembly comprising a sleeve assembly, a target rod, a target, and a packing gland housing; said target attached to said target rod; said packing gland housing proximate said second end of said shell assembly; said target rod connected to said actuator piston; and said second end of said shell assembly connected to an opening in a pipe wall of a pipe;
    extending said target rod and said target through said side opening into said pipe interior such that said target is oriented generally normal to a flow of said high-pressure high-velocity fluid;
    waiting a predetermined length of time;
    retracting said target rod and said target from said pipe interior; and
    evaluating a quantity of pits on said target to assessing the cleanliness of said high-pressure high-velocity fluid in said pipe.

12. The method as in claim 11, further comprising said pipe being oriented between a first set of conduits to be cleaned and a second conduits to be cleaned by said high-pressure high-velocity fluid.

13. The method as in claim 11, wherein:
    said packing gland housing comprising a packing, a packing gland, and a packing gland housing flange;
    said packing oriented within said packing gland housing;
    said packing surrounding a circumference of and contiguous with said target rod;
    said packing gland pressing said packing against said target rod; and
    said target rod being slidingly movable through said packing and through said pipe wall opening into an interior of said pipe.

14. The method as in claim 13, further comprising:
    a valve having a first end and second end;
    said first end of said valve connected to said pipe wall opening;
    said packing gland housing connected to said second end of said valve; and
    said target rod being slidingly movable through a valve channel interior said valve and through said pipe wall opening into said interior of said pipe.

15. The method as in claim 14, said valve being remotely operable.

16. The method as in claim 14, said pipe wall opening comprising a flange capable of attaching to said first end of said valve.

17. The method as in claim 11, further comprising:
- a flag bolt slot oriented along a longitudinal axis of said sleeve assembly;
- a flag bolt traversing through said flag bolt slot and connecting to an actuator/rod coupling;
- said actuator/rod coupling connecting said target rod and said actuator piston;
- wherein said flag bolt is oriented proximate said second end of said shell assembly when said target rod is inserted into said pipe interior; and
- said flag bolt is oriented proximate said first end of said shell assembly when said target rod is withdrawn from said pipe interior.

18. The method as in claim 13, said actuator further comprising a remotely controlled pneumatic controller capable of extending and retracting said target into said pipe interior.

19. The method as in claim 11, further comprising accessing said target through a target access void in said sleeve assembly.

20. A method of assessing the cleanliness of a high-pressure high-velocity fluid in a pipe, comprising:
- connecting a high-pressure target inserter to a side opening in a pipe having a pipe interior under high-pressure, said target inserter comprising a target rod and a target;
- extending said target rod and said target through said side opening into said pipe interior such that said target is oriented generally normal to a flow of said high-pressure high-velocity fluid;
- waiting a predetermined length of time;
- retracting said target rod and said target from said pipe interior; and
- evaluating a quantity of pits on said target to assess a cleanliness of an upstream set of conduits being cleaned by said high-pressure high-velocity fluid.

* * * * *